(12) United States Patent
Gerstenhaber

(10) Patent No.: US 7,960,497 B2
(45) Date of Patent: Jun. 14, 2011

(54) PREPARATION OF ALKYL KETENE DIMERS

(75) Inventor: David A. Gerstenhaber, Newark, DE (US)

(73) Assignee: Hercules Incorporated, Wilmington, DE (US)

( * ) Notice: Subject to any disclaimer, the term of this patent is extended or adjusted under 35 U.S.C. 154(b) by 934 days.

(21) Appl. No.: 11/649,005

(22) Filed: Jan. 3, 2007

(65) Prior Publication Data

US 2007/0173579 A1 Jul. 26, 2007

Related U.S. Application Data

(60) Provisional application No. 60/755,966, filed on Jan. 3, 2006.

(51) Int. Cl.
*C07C 45/85* (2006.01)
*C07C 45/89* (2006.01)
*C07C 305/12* (2006.01)

(52) U.S. Cl. ........ 528/332; 528/271; 528/363; 549/329; 568/301; 568/302

(58) Field of Classification Search .................. 528/271, 528/332, 363; 549/329; 568/301, 302
See application file for complete search history.

(56) References Cited

U.S. PATENT DOCUMENTS

| 5,344,943 A | 9/1994 | Brolund | 549/329 |
| 5,399,774 A | 3/1995 | McIntosh | 568/301 |
| 5,502,218 A | 3/1996 | Nicholass et al. | 549/329 |
| 5,672,721 A | 9/1997 | Ettl | 549/329 |

FOREIGN PATENT DOCUMENTS

| EP | 0 550 107 | 12/1992 |
| EP | 0 612 739 | 2/1994 |

*Primary Examiner* — Ana L Woodward
(74) *Attorney, Agent, or Firm* — Joanne Mary Fobare Rossi

(57) ABSTRACT

The embodiments of the process of the present invention relate to the preparation of alkyl ketene dimers (AKD), where the process combines at least one polyamine with a fatty acid chloride in a molar ratio of less than one mole of polyamine to one mole of fatty acid chloride thereby forming an alkyl ketene dimer/amine salt that is subsequently separated into an organic dimer layer and an aqueous salt layer.

16 Claims, No Drawings

PREPARATION OF ALKYL KETENE DIMERS

This application is a regular US application which takes priority from provisional application 60/755,966, filed Jan. 3, 2006 the contents of which are incorporated by reference.

FIELD OF THE INVENTION

The embodiments of the present invention relate to a process for the preparation of alkyl ketene dimers for paper applications.

BACKGROUND OF THE INVENTION

Alkyl ketene dimers (AKD) are typically utilized as sizing products in the pulp and paper industry. To this end AKDs, a waxy, water-insoluble substance, are usually added usually in the form of aqueous dispersions comprising cationic starch or cationic synthetic polymers as dispersing agents in the paper making process.

A common procedure used in the preparation of AKD includes the addition of fatty acid chlorides (FAC) (typically having structures of the general formula $CH_3(CH_2)_nCOCl$ where n is an integer ranging from 8 to 20) to a heated mixture of triethylamine (TEA) and an inert solvent(s). Typical processes require the presence of the inert solvent to dilute the above-described slurry to ensure good mixing and product separation. In the absence of the inert solvent, the reaction viscosity of the FAC amine mixture increases as a TEA-Cl salt by-product forms. It is the formation of this by-product in the FAC amine mixture which makes effective mixing of the reactants and removal of the final AKD product difficult to effectively achieve. Examples of typical solvents utilized in the preparation of AKD are propylene dichloride and toluene.

Attempts have been made in the industry to reduce or remove the solvents from the AKD formation process whereby either the dilution solvent has been replaced by an excess amount of tertiary amine or through the use of rigorous distillation. Typically, the resultant AKD is isolated by filtering the solvent/AKD solution where the remaining solvent in the AKD fraction is reduced via distillation. However, such processes, including those utilizing distillation steps, remain problematic because trace amounts of solvent remain in the final product.

U.S. Pat. No. 5,672,721 teaches the production of AKD with low amounts of solvent by using a water immiscible inert solvent followed by a two-stage distillation step followed by the addition of water or steam.

U.S. Pat. No. 5,344,943 teaches a process for the preparation of long-chain alkyl ketene dimers in the absence of additional organic solvents through the use of a molar excess of triethyl amine to fatty acid chloride. The process requires the use of intensive mixing to generate high shear rates which controls the viscosity of the reaction mixture. This process is difficult to practice at the larger scales needed for commercial production of AKD products.

U.S. Pat. No. 5,399,774 teaches the use of tertiary amines as both a reactant and as a diluent. In this use, at least 1.15 moles of amine is used per mole of fatty acid chloride to make AKD. Amines useful in the process may be either monoamines or diamines. The process described teaches stripping tertiary amine hydrogen halide crystals formed in the production of AKD with an acid. Care must be taken when using the acid so as not to hydrolyze the AKD with the acid U.S. Pat. No. 5,502,218 teaches the solventless production of alkyl ketene dimers which uses pre-prepared crystals of tertiaryamine hydrogen halide as a diluent in the production of AKD products, where the tertiary amines are used in a stoichiometric to molar excess amount relative to the amount of fatty acid chloride used.

There still remains a need to have a process for the manufacture of AKD products which is able to be performed on a commercial scale and which results in a final AKD product which has a sufficiently low level of residual solvent.

The use of solvents in the preparation of AKD creates a problem due to environmental concerns regarding the presence of residual halogenated and/or low boiling solvents in the final AKD product.

These residual solvents pose a problem for the papermaking industry by requiring papermills to make the necessary accommodations for the solvent as it escapes in the exhaust from during drying operations. Also, solvent will be present in effluent produced by the papermills.

Additionally, the residual solvent may be present in the cellulosic products containing the AKD product. The presence of these residual solvents may limit the end uses for these cellulosic products and make their use inappropriate for endproducts which are required to be essentially free of any residual solvents, such as for example for packaging for food contact.

Thus, a heretofore-unaddressed need exists in the industry to provide processes for the preparation of AKD without the addition of solvents which ultimately remain in detectable levels in the final AKD product and cellulosic products treated with AKD products.

SUMMARY OF THE INVENTION

The present invention relates to a process for the preparation of alkyl ketene dimers, comprising the steps in sequence of:

(a) charging a polyamine catalyst to a reaction vessel, and then heating the polyamine to a temperature ranging from about 50° C. to about 70° C.;

(b) charging a fatty acid chloride to the reaction vessel containing the polyamine over a time period ranging from about 30-90 minutes, thereby forming a reaction mixture comprising an alkyl ketene dimer/amine salt;

(c) adding an amount of water to the reaction mixture wherein an organic alkyl ketene dimer layer and an aqueous salt layer are formed;

(d) separating the organic alkyl ketene dimer layer and the aqueous salt layer, wherein the polyamine used in the process is present in amounts ranging from about 0.5 to less than about 1.0 equivalents per mole equivalent of fatty acid.

DETAILED DESCRIPTION

The embodiments of the present invention describe a process for the preparation of alkyl ketene dimers (AKD), wherein a AKD product contains significantly low levels of residual solvent(s), the process comprising:

(a) charging a polyamine to a reaction vessel and heating the amine to a temperature ranging from about 50° C. to about 70° C., preferably ranging from about 50° C. to about 65° C., more preferably ranging from about 55° C. to about 65° C., most preferably about 65° C.;

(b) charging a fatty acid chloride to the reaction vessel over a time period ranging from about 30-90 minutes, preferably about 35 to about 40 minutes, most preferably 40 minutes, wherein the fatty acid chloride is used in amounts in excess of 1.0 molar equivalents relative to the amine, thereby forming a reaction mixture comprising an alkyl ketene dimer/amine salt;

(c) adding an effective amount of water to the reaction mixture to form an alkyl ketene dimer layer and an aqueous salt layer in the reaction mixture;

(d) optionally heating the reaction mixture to a temperature ranging from about 90° C. to about 105° C.; and (e) separating the organic alkyl ketene dimer layer and the aqueous salt layer.

wherein the polyamine is present in amounts ranging from about 0.5 to about less than 1.0 equivalents per mole equivalent of fatty acid chloride, preferably ranging from about 0.5 to about 0.95 equivalents, more preferably ranging from 0.6 to less than 0.95 equivalents.

The process for the preparation of AKD may be performed in a batch, semi-batch or continuous manner.

While not wishing to be bound by theory, the following depicts a generalized mechanism for AKD formation of the present invention.

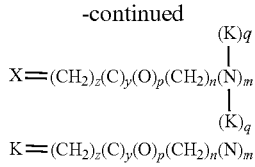

$n = 0$ to $1$
$m = 0$ to $1$
$z = 0$ to $6$
$y = 0$ to $1$
$p = 0$ to $1$
$q = 0$ to $1$ wherein the values of n, m, z, y and q can be the same or different and the sum of the values of n, m, z, y and q is greater than 1 and wherein the amines contain one or more heteroatomic rings, each of which may contain two or more tertiary amines per ring, wherein these amines may also further contain one or both of a carbonyl unit or ether linkage, forming an

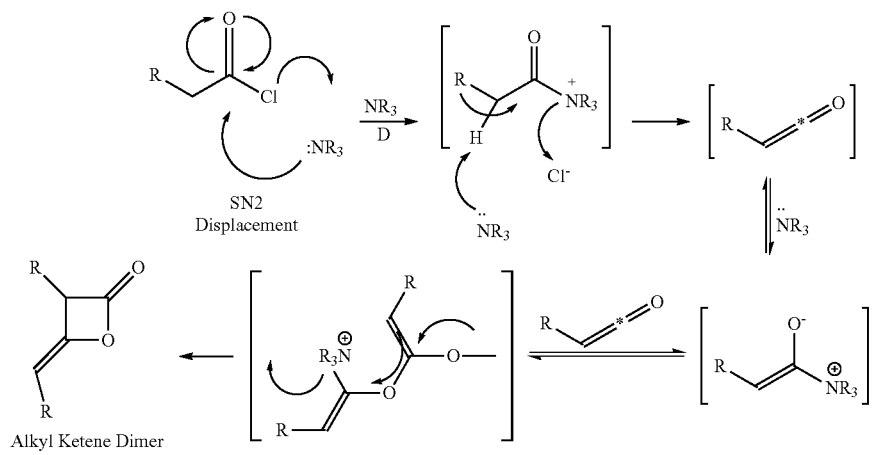

Alkyl Ketene Dimer

The embodiments of the present invention provide for the preparation of AKD through the use of tertiary polyamines, more particularly bi- and tri-cyclic tertiary amines and polar tertiary amine, wherein the process is performed with low levels or more particularly, in the absence of halogenated or volatile organic solvents.

In the embodiments of the present invention, the polyamine may be at least one of the polyamines that are tertiary cyclic amines which can be polycyclic straight-chain or branched.

Typically, the tertiary polycyclic amine may be a polycyclic tertiary amine comprising moieties containing polar functional groups. These amines are highly reactive due to their particular steric considerations and through chemical assistance available through the polar functionality.

Tertiary cyclic polyamines suitable for use with the embodiments of the present invention include those having the general structure:

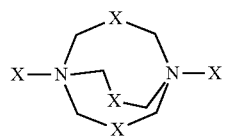

ether, ester or acetate functionality within the moiety. The cyclic polar amines can act as both a reactive amine and a diluent for in the preparation of AKD.

Examples of preferred tertiary cyclic polyamines include, but are not limited to, tropinone, quinuclidinyl acetate and 4-[2-dimethylamino)amino)ethyl]-morpholine. More preferably, the cyclic polar amine is tropinone and quinuclidinyl acetate, and most preferably tropinone. While not wishing to be bound by theory, these examples show the presence of two "arms" of the amine pinned back to expose a nitrogen lone pair of electrons. These electrons are better suited to participate in the SN2 displacement of the FAC and formation of the AKD. The polar ketone and the acetate group of tropinone and quinuclidinyl acetate, respectively, further improve the reaction rate of the formation of AKD as each of these groups facilitates the formation of a polar charged amide intermediate.

The polyamines are utilized in the production of AKD because of the inherent basicity of the tertiary amine functionality while utilizing the additional amines present in the polyamine and the hydrocarbon backbones (per mole of material) of the polyamine for improved reactivity and lower reaction viscosity of the reaction mixture comprising AKD and amine salt.

Typically, useful polyamines are of the structure $R_1R_2R_3N$, where R is an alkyl or alkenyl chain containing one or more repeating tertiary unit. $R_1$, $R_2$ and $R_3$ can be separate or connected forming one or two heteroatomic rings. While not wishing to be bound by theory the polyamine structures contain two alkyl "arms" on the reactive amines that are pinned back, thereby exposing a nitrogen lone pair of electrons, where the electrons are better suited to participate in the SN2 displacement of the FAC and formation of the AKD.

Preferred cyclic polyamines suitable for use with the embodiments of the present invention are those having the general structure:

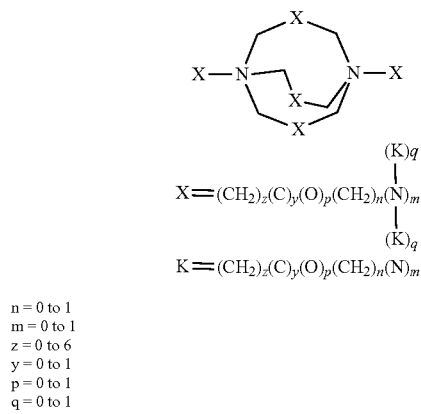

n = 0 to 1
m = 0 to 1
z = 0 to 6
y = 0 to 1
p = 0 to 1
q = 0 to 1 wherein the structures contain one or more heteroatomic rings, each of which may contain two or more tertiary amines per ring and wherein the values of m, n, z, y and q can be the same or different and the sum of the values of m, n, z, y and q is greater than zero. The cyclic polyamines can act as both a reactive amine and as a diluent for the reaction mixture comprising AKD and amine salt.

Non-limiting examples of preferred cyclic polyamines include 1,4-diazabicyclo[2.2.2]octane, hexamethyltetramine, 1,4-dimethyl piperazine and 4,4'-trimethylenebis(1-methyl-piperidine). Most preferably, the cyclic polyamine is 1,4-dimethyl piperazine.

Furthermore, the cyclic polyamines useful in the present invention must be in a liquid state at the operating temperature of the process for the preparation of AKD.

Typical straight-chain tertiary polyamines suitable for use in the embodiments of the present invention include those having the general structure:

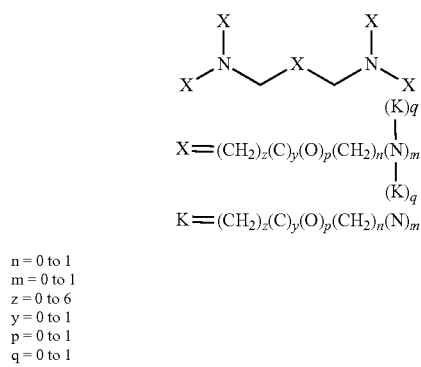

n = 0 to 1
m = 0 to 1
z = 0 to 6
y = 0 to 1
p = 0 to 1
q = 0 to 1 and where the typical branched-chain tertiary polyamines suitable for use in the embodiments of the present invention include those having the general structure

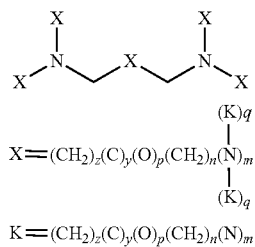

n = 0 to 1
m = 0 to 1
z = 0 to 6
y = 0 to 1
p = 0 to 1
q = 0 to 1 where n, m, z, y and q may be the same or different values and the sum of n, m, z, y and q is greater than zero and where the structures contain two or more tertiary amines connected via an alkyl chain comprising one or more carbon units, which may also contain one or both of a carbonyl unit or ether linkage, forming ester, acetate or ether functionality within the moiety. The branched tertiary polyamines can act as both a reactive amine in the formation of AKD and as a diluent for the resultant AKD/amine salt reaction mixture.

Examples of suitable branched tertiary polyamines include, but are not limited to, N,N,N',N'',N''',N'''-hexamethylethylenetetramine; N,N,N'',N''-tetramethyl-1,6-hexanediamine; N,N,N',N''N''-pentamethyldiethylenetriamine; N,N,N'',N''-tetramethyl-1,3-propanediamine; N,N,N'',N''-tetraethylethylenediamine; N,N,N'',N''-tetramethylethylenediamine and N,N,N'',N''-tetramethylmethylenediamine. Preferred examples include N,N,N'',N''-tetramethyl-1,6-hexanediamine; N,N,N',N''N''-pentamethyldiethylenetriamine; N,N,N'',N''-tetramethyl-1,3-propanediamine; N,N,N'',N''-tetraethylethylenediamine. The most preferred branched tertiary polyamines are N,N,N'',N''-tetramethyl-1,6-hexanediamine and N,N,N',N''N''-pentamethyldiethylenetriamine.

Examples of suitable straight-chain tertiary polyamines include, but are not limited to 2,4-dimethyl-2,4-diazapentane, 2,5-dimethyl-2,5-diazahexane, 1,1'-(1,2-ethanediyl)bis[piperidine], N,N,N', N'-tetramethyl-1,2-diaminocyclohexane, 1,4-dimethyl-1,4-diazacyclohexane, diazabicyclo[2.2.2]octane, 2,6-dimethyl-2,6-diazaheptane, 2,7-dimethyl-2,7-diazaoctane, 2,7-dimethyl-2,7-diaza-4-octene, 2,7-dimethyl-2,7-diaza-4-octyne, 2,9-dimethyl-2,9-diazadecane, and 2,5,8,11-tetramethyl-2,5,8,11-tetraazadodecane.

With the straight-chain and branched tertiary polyamines, as with the cyclic amine moieties, the inherent basicity of the tertiary amine functionality, additional amines and hydrocarbon backbones (per mole of material) provide improved reactivity of the polyamine and lower reaction viscosity of the resultant AKD/amine salt reaction mixture. For example, branched tertiary polyamines like N,N,N'',N''-tetramethyl-1,6-hexanediamine, the larger (e.g. $C_6$) hydrocarbon backbone allows the polyamine to acquire solvent-like properties, which assists in reducing the viscosity of the resultant AKD/amine salt reaction mixture.

Typical fatty acid chlorides suitable for use with the embodiments of the present invention are those having the general structure:

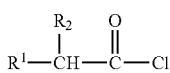

wherein R1 is $C_7$ to $C_{30}$ alkyl or $C_7$ to $C_{30}$ alkenyl and R2 is hydrogen or $C_1$ to $C_8$, more preferably R1 is $C_{10}$ to $C_{22}$ and R2 is hydrogen.

The fatty acid chloride can have up to 30 carbon atoms, suitably with from 12 to 22 carbon atoms and preferably with from 16 to 18 carbon atoms, or a mixture of such fatty acid chlorides. The fatty acid chloride can be either a saturated or unsaturated fatty acid chloride and as some examples can be chlorides of lauric acid, myristic acid, palmitic acid, stearic acid, arachidic acid, palmitoleic acid, oleic acid etc. Chlorides of naturally occurring fatty acids such as those from coco and tallow can of course also be used. Stearic acid chloride is particularly preferred.

Once the reaction is complete an effective amount of water chilled to about 39° C. to about 45° C. is quickly charged to the reaction mixture, wherein the internal temperature of the reactor drops quickly below the freezing point of the AKD, thereby producing a waxy solid. Thus, the AKD is separated from the water layer which reduces the available surface area of the AKD to further protect the dimer from hydrolysis by limiting its contact with water. Reheating the reaction mixture to a temperature ranging from about 90° C. to about 105° C. melts the AKD, thereby facilitating a liquid/liquid separation of the AKD from residual amine salt present in the reaction mixture.

Optionally, as well as adding an effective amount of water to the reaction mixture, an acid treatment comprising treating the reaction mixture with aqueous inorganic acid may also be performed to aid in the removal of any residual amine from the reaction mixture. The concentration of the aqueous inorganic acid is dependent on the amount of polyamine remaining in the reaction mixture. One of the advantages of the present process is that since the polyamine is present in amounts ranging from about 0.5 to about less than 1.0 equivalents per mole equivalent of fatty acid chloride, treatment of the reaction mixture with the aqueous inorganic acid to remove excess polyamine is typically not necessary.

One advantage of the method of the present invention is the high dimer assays that are attainable in the reaction mixture. Through the use of the method of the present invention, almost ketene dimer assays of greater than 60%, preferably greater than 80%, more preferably greater than 90% of the final AKD product when isolated and analyzed using standard IR, SEC and NMR techniques.

Typical methods for separating AKD from the amine salts used by those skilled in the art generally employ one of three techniques: 1) solvent filtration of soluble AKD from the insoluble amine, salts, 2) centrifugation of the amine salts from the solvent solubilized AKD and 3) acid extraction of the amine salts from solvent solubilized AKD.

As the method described herein relies only upon the ability of the amine to act as a solvent and no additional solvent is added in the production of AKD, it is essentially a solventless method. The final AKD product produced by this method contains minimal amounts of solvent.

Where a range of numerical values is recited herein, unless otherwise stated, the range is intended to include the endpoints thereof, and all integers and fractions within the range. It is not intended that the scope of the various embodiments of the invention be limited to the specific values recited when defining a range. Moreover, all ranges set forth herein are intended to include not only the particular ranges specifically described, but also any combination of values therein, including the minimum and maximum values recited.

Description of Analytical Procedures

An infrared (IR) spectroscopy method is used for the determination of alkylketene dimer assay values. The alkylketene dimer sample is dissolved in heptane, extracted with a water/methanol mixture (to remove polar impurities that give a positive interference), and the IR spectrum scanned. The carbonyl absorbance, relative to the absorbance of standards similarly prepared, is used to quantitate the alkylketene dimer assay.

A size-exclusion chromatography (SEC) method is used for measuring the fraction of species higher in molecular weight than alkylketene dimer. The alkylketene dimer sample is dissolved in tetrahydrofuran (THF) and chromatographed at 40° C. A differential refractive index (DRI) detector is used. The alkylketene dimer elutes as a single peak. The area percent of the fraction higher in molecular weight is reported.

Nuclear magnetic resonance (NMR) spectroscopy is used to quantitate the byproducts and process impurities present in alkylketene dimer samples. The sample and internal standard, triphenylphosphine oxide (TPPO), are dissolved in d-chloroform, and the proton spectrum obtained. The impurities, other than those quantitated as described in [00036], are calculated on an absolute weight basis.

EXAMPLES

The embodiments of the present invention are further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the invention to adapt it to various uses and conditions. Thus various modifications of the present invention in addition to those shown and described herein will be apparent to those skilled in the art from the foregoing description. Although the invention has been described with reference to particular means, materials and embodiments, it is to be understood that the invention is not limited to the particulars disclosed, and extends to all equivalents within the scope of the claims.

Generally, in the Examples described herein, the reactor assemblies comprised a jacketed resin kettle having an internal capacity of 50 to 1000 milliliters. Each reactor assembly was equipped with a 4-neck kettle head and a Teflon® stopcock for draining the reactor contents. Each vessel was also equipped with a Teflon anchor controlled via an overhead stirrer, a cold water condenser with gas bubbler, a y-tube, thermocouple, nitrogen inlet, rubber septa and a stopper. The glassware was dried in an oven at 105° C. for 1 to 2 hours and flushed with nitrogen overnight.

Example 1

1.0/0.6 Mole Ratio Fatty Acid Chloride 364/N,N,N', N'-tetramethyl-1,6-hexanediamine The vessel was charged with N,N,N',N'-tetramethyl-1,6-hexanediamine (12.1 g, 70.22 mmol) and heated to 65° C. with a water circulation bath while stirring and blanketing with nitrogen. Once an internal temperature of 65° C. was achieved, the addition of fatty acid chloride 364 (34.7 g, 119.64 mmol) was started via syringe pump through one of the septa. The fatty acid chloride was added at an even rate over 40 minutes to maintain the reaction temperature between 60 and 65° C. Once the addition was complete, the hot water in the bath was replaced with ice water. The reaction slurry was treated with chilled 37.5% HCl (10.2 g, 105 mmol) plus de-ionized water (29.7 g). Once the temperature was cooled to 45° C. the cold water bath was replaced with hot water to heat the reaction rapidly back to 90° C. Once the slurry was heated to 90° C. for separation the crude reaction product was isolated and analyzed using standard IR, SEC and NMR techniques and data to determine that the alkyl ketene dimer assay was 94.0%.

Example 2

1.0/0.6 Mole Ratio Fatty Acid Chloride 291/N,N,N',N'-tetramethyl-1,6-hexanediamine To the vessel was charged N,N,N',N'-tetramethyl-1,6-hexanediamine (11.3 g, 65.6 mmol) and heated to 65° C. Fatty acid chloride 291 (35.0 g 115.7 mmol) was added at an even rate over 35 minutes. When the addition was complete, the hot water in the bath was replaced with ice water. 5 minutes after the fatty acid chloride was added, 37.5% $HCl_{(aq)}$ (9.7 g, 99 mmol) plus 27.6 g of de-ionized water were combined, chilled and added to the reaction while cold water was circulated to cool it. When the temperature reached 45° C., the cold water in the bath was replaced with hot water in order to heat the reaction to 90° C. Once the reaction reached 65° C. the stirring was slowed to a minimum speed. Once the slurry was heated to 90° C. for separation the crude reaction product was isolated and analyzed using standard IR, SEC and NMR techniques. It was determined that alkyl ketene dimer assay was 92.5%.

Example 3

1.00/0.94 Mole Ratio Fatty Acid Chloride 532/N,N,N',N'-tetramethyl-1,6-hexanediamine The reaction assembly was the same as stated above (Example 2) except that an addition funnel wrapped with heating tape was used to add the fatty acid chloride instead of a syringe pump. To the reaction vessel was charged tetramethyl-1,6-hexanediamine (15.9 g, 92.3 mmol) and heated to 63° C. with a water circulation bath. Once the tetramethyl-1,6-hexanediamine was at reaction temperature, liquid fatty acid chloride 532 (34.3 g, 98.7 mmol), was charged over a period of 90 minutes. When the addition was complete, the hot water in the bath was replaced with ice and cold water. Six minutes after the addition was complete 37.5% HCl (13.4, 138 mmol) and cold de-ionized water (39.1 g) was charged. When the temperature reached 35° C., the cold water in the bath was replaced with hot water in order to heat the reaction to 90° C. Once the slurry was heated to 90° C. for separation, the crude reaction product was isolated and analyzed using standard IR, SEC and NMR techniques. It was determined that the alkyl ketene dimer assay was 88.1%.

Example 4

1.00/0.6 Mole Ratio Fatty Acid Chloride 364/N,N,N',N'-pentamethyldiethylenetriamine The procedure for this reaction was the same as Example 1. To the reaction vessel, in a manner analogous to Example 1, was charged fatty acid chloride 364 (34.7 g, 116.64 mmol), pentamethyldiethylenetriamine (12.3 g, 70.98 mmol), 37.5% HCl (10.2 g, 105 mmol) and de-ionized water (30.2 g). Once the slurry was heated to 90° C. for separation the crude reaction product was isolated and analyzed using standard IR, SEC and NMR techniques. It was determined that the alkyl ketene dimer assay was 85.5%.

Example 5

1.0/0.95 Mole Ratio Fatty Acid Chloride 291/N,N,N',N'',N''-pentamethyldiethylenetriamine The procedure for this reaction was the same as Example 2. To the reaction vessel, in a manner analogous to Example 2, was charged fatty acid chloride 364 (30.0 g, 99.2 mmol), pentamethyldiethylenetriamine (16.5 g, 95.2 mmol), 37.5% HCl (13.7 g, 141 mmol) and de-ionized water (40.8 g). Once the slurry was heated to 90° C. for separation, the crude reaction product was isolated and analyzed using standard IR, SEC and NMR techniques. It was determined that the alkyl ketene dimer assay was 80.2%.

Example 6

1.0/0.6 Mole Ratio Fatty Acid Chloride 364/N,N,N',N'',N''-pentamethyldipropylenetriamine The procedure for this reaction was the same as Example 1. To the vessel, in a manner analogous to Example 1, was charged fatty acid chloride 364 (34.7 g, 119.6 mmol), pentamethyldiethylenetriamine (14.1 g, 70.0 mmol), 37.5% HCl (10.2 g, 105 mmol) and de-ionized water (36.3 g). Once the slurry was heated to 90° C. for separation the crude reaction product was isolated and analyzed using standard IR, SEC and NMR techniques. It was determined that the alkyl ketene dimer assay was 85.0%.

Example 7

1.0/0.6 Mole Ratio Fatty Acid Chloride 291/N,N,N',N'-tetramethyl-1,3-propanediamine The procedure for this reaction was the same as Example 2. To the vessel, in a manner analogous to Example 2, was charged fatty acid chloride 291 (35.0 g, 115.73 mmol), tetramethyl-1,3-propanediamine (8.6 g, 66.03 mmol), 37.5% HCl (9.6 g, 99 mmol) and de-ionized water (18.8 g). Once the slurry was heated to 90° C. for separation the crude reaction product was isolated and analyzed using standard IR, SEC and NMR techniques. It was determined that the alkyl ketene dimer assay was 65.9%.

Example 8

1.0/0.6 Mole Ratio Fatty Acid Chloride 364/tetraethylethylenediamine

The procedure for this reaction was the same as Example 1. To the reaction vessel, in a manner analogous to Example 1, was charged fatty acid chloride 364 (34.7 g, 117 mmol), tetraethylethylenediamine (12.3 g, 71.3 mmol), 37.5% HCl (10.2 g, 105 mmol) and de-ionized water (30.4 g). Once the slurry was heated to 90° C. for separation the crude reaction product was isolated and analyzed using standard IR, SEC and NMR techniques. It was determined that the alkyl ketene dimer assay was 74.5%.

Other systems, methods, process and advantages of the embodiments of the present invention will be or become apparent to one skilled in the art upon examination of the detailed description. It is intended that all such additional systems, methods, processes and advantages be included within this description, be within the scope of the present invention, and be protected by the accompanying claims.

What is claimed is:

1. A process for the preparation of alkyl ketene dimers, comprising in sequence the steps of:
   (a) charging a polyamine to a reaction vessel, and then heating the polyamine to a temperature ranging from about 50° C. to about 70° C.;
   (b) charging a fatty acid chloride to the reaction vessel containing the polyamine over a time period ranging from about 30-90 minutes, thereby forming a reaction mixture comprising an alkyl ketene dimer/amine salt;
   (c) adding an amount of water to the reaction mixture wherein an organic alkyl ketene dimer layer and an aqueous salt layer are formed;
   (d) separating the organic alkyl ketene dimer layer and the aqueous salt layer,
wherein the polyamine used in the process is present in amounts ranging from about 0.5 to less than 1.0 equivalents per mole equivalent of fatty acid chloride.

2. The process according to claim 1, wherein the polyamine of step (a) is selected from the group consisting of a tertiary cyclic polyamine comprising moieties containing ether, ester or acetate functional groups; straight-chain tertiary polyamine and branched tertiary polyamines.

3. The process according to claim 2, wherein the straight-chain tertiary polyamines are selected from the group consisting of 2,4-dimethyl-2,4-diazapentane, 2,5-dimethyl-2,5-diazahexane, 1,1'-(1,2-ethanediyl)bis[piperidine], N,N,N',N'-tetramethyl-1,2-diaminocyclohexane, 1,4-dimethyl-1,4-diazacyclohexane, diazabicyclo[2.2.2]octane, 2,6-dimethyl-2,6-diazaheptane, 2,7-dimethyl-2,7-diazaoctane, 2,7-dimethyl -2,7-diaza-4-octene, 2,7-dimethyl-2,7-diaza-4-octyne, 2,9-dimethyl-2,9-diazadecane, and 2,5,8,11-tetramethyl-2,5,8,11-tetraazadodecane.

4. The process according to claim 2, wherein the branched tertiary polyamines are selected from the group consisting of N,N,N',N",N"',N"''-hexamethylethylenetetramine; N,N,N",N"-tetramethyl-1,6-hexanediamine; N,N,N',N"N"-pentamethyldiethylenetriamine; N,N,N",N"-tetramethyl-1,3-propanediamine; N,N,N",N"-tetraethylethylenediamine; N,N,N",N"-tetramethylethylenediamine and N,N,N",N"-tetramethylmethylenediamine.

5. The process according to claim 1, wherein the polyamine(s) are tertiary cyclic polyamine comprising moieties containing ether, ester or acetate functional groups.

6. The process according to claim 1, wherein the polyamine is tropinone, quinuclidinyl acetate or 4-[2-dimethylamino) amino) ethyl]-morpholine.

7. The process according to claim 1, wherein the polyamine of step (a) comprise cyclic polyamines.

8. The process according to claim 7, wherein the cyclic polyamine is selected from the group consisting of 1,4-diazabicyclo[2.2.2]octane, 1,4-dimethyl piperazine and 4,4'-trimethylenebis(1-methyl-piperidine).

9. The process according to claim 1, wherein the fatty acid chloride comprises stearoyl chloride.

10. The process according to claim 1, wherein the polyamine comprises 1,4-dimethyl piperazine and the fatty acid chloride is stearoyl chloride.

11. The process according to claim 1, wherein the temperature in step (a) ranges from about 50° C. to about 65° C.

12. The process according to claim 11, wherein the temperature in step (a) ranges from about 55° C. to about 65° C.

13. The process according to claim 12, wherein the temperature in step (a) is about 65° C.

14. The process according to claim 1, wherein the fatty acid chloride is charged to the reaction vessel over a time period ranging from about 35 to about 40 minutes.

15. The process according to claim 14, wherein the fatty acid chloride is charged to the reaction vessel over a time period of about 40 minutes.

16. An alkyl ketene dimer produced according to the process of claim 1.

* * * * *